US005750412A

United States Patent [19]

Sucholeiki

[11] Patent Number: 5,750,412
[45] Date of Patent: May 12, 1998

[54] PARAMAGNETIC SCINTILLATION PARTICLES AND ASSAY

[75] Inventor: Irving Sucholeiki, Watertown, Mass.

[73] Assignee: Solid Phase Sciences Corporation, Watertown, Mass.

[21] Appl. No.: 699,796

[22] Filed: Aug. 19, 1996

Related U.S. Application Data

[60] Provisional application No. 60/002,831 Aug. 25, 1995.
[51] Int. Cl.$^6$ .................. G01N 33/553; G01N 33/543; G01N 33/546; G01N 33/542
[52] U.S. Cl. .............. 436/525; 436/523; 436/533; 436/537; 436/546; 436/805
[58] Field of Search .................. 436/525, 523, 436/533, 537, 546, 808

[56] References Cited

U.S. PATENT DOCUMENTS 4,650,770  3/1987  Liu et al. .................. 436/523

FOREIGN PATENT DOCUMENTS

WO 89/04373  5/1989  WIPO .

OTHER PUBLICATIONS

Harlow, et al.: Antibodies a laboratory manual: pp. 591–592, 1988.
Kaplan, et al.: Clinicla Chemistry theory, analysis, and correlation: pp. 145–151, 1984.

Primary Examiner—Laurie Scheiner
Assistant Examiner—Brett Nelson
Attorney, Agent, or Firm—Timothy J. Shea, II; Jacob N. Erlich

[57] ABSTRACT

An immunoscintillating composition and method of radioimmunoassay is disclosed whereby polymer coated paramagnetic particles and binding agent such as an antibody are associated by chemical or physical means to provide solid scintillating immunoadsorbent particles which are paramagnetic. These particles are capable of selectively binding or retaining radioactive or labeled antigens or ligands and transmitting radioactive energy to a phosphor or photon emitting substance that is bound by chemical or physical means to the particles. Upon binding of the antigens or ligands to the surface of the particles the particles are separated from the unbound components in solution by application of a magnetic field. The luminescence emitted by the phosphor which is attached to the magnetically separated particles is measured by a scintillator counter and is directly proportional to the radioactive energy released by the labeled antigen bound to the antibody. Upon completion of the measurement the paramagnetic particles can be magnetically separated and the labeled antigens or ligands removed for further analysis and the particles recycled for use in other assays.

26 Claims, No Drawings

PARAMAGNETIC SCINTILLATION PARTICLES AND ASSAY

This application claims priority to provisional application No. 60/002,831 filed on Aug. 25, 1996.

BACKGROUND OF THE INVENTION

1. Field of the invention

The invention resides in the field of analytical biochemistry and more particularly relates to radioimmunochemistry.

2. Description of the prior art

A typical method for measuring the binding of antigens or ligands to proteins is particle agglutination or precipitation. In such a method a protein bound suspension of beads or particles reacts with some antigen or ligand, causing the particles to flocculate or precipitate. Quantitation is accomplished through the use of spectrophotometery to measure the change of light transmission through the medium. Another method, which is far more sensitive, is the use of radioactivity in the measurement. In such a method, either the ligand or the protein is radiolabeled and complexed with either unlabeled protein or ligand, respectively. The radiolabeld complex is then separated from unbound material by precipitation followed by centrifugation. One problem with this approach is that the washing of the precipitant is not very efficient and requires many repeated washes and centrifugation steps. This invariably produces large amounts of radioactive waste. If the protein or ligand is bound to an insoluble particle, then the unbound material may be separated from the bound complex by simple filtration.

Filtration of insoluble particles incorporating a protein ligand complex is efficient when large numbers of particles are employed, yet can be difficult when small numbers of particles are used. In cases where small numbers of particles are used, other insoluble supports are utilized, such as paramagnetic particles. Exposure of antibody-bound paramagnetic particles to a magnetic field can be used to separate antibody-bound antigen from unbound antigen in immunoassays (see M. Okada, Y. Ashihara, A. Yano, M. Oishi, K. Yoshioka, T. Nakamura, U.S. Pat. No. 5,320,944 and C. H. J. Wang, D. O. Shah, U.S. Pat. No. 5,283,079).

Such materials are attracted to a magnetic field and this attraction is used to separate the bound protein-ligand complex from the surrounding liquid medium. Magnetic separation methods have also been applied successfully in cell sorting. A definite advantage that magnetic separation has over simple filtration is the ability to separate out small numbers of particles from small reaction volumes. Another advantage is the ease to which magnetic separation can be automated, as compared to standard filtration.

Known magnetically separable beads or particles have several short-comings as a separation support system. First the beads or particles swell or contract or dissolve depending upon the solvent and temperature conditions. Further, it is taught that swollen beads lose their metal oxide particles into the reaction solution and thus become unresponsive to magnetic separation. To counteract metal oxide loss due to swelling, polymeric beads are frequently composed of polymers that are highly cross-linked. As a result, only the exterior of the bead is available for binding or derivatization. Thus, the loading of the bead is reduced. A solution to this has been the development of a solvent stable, paramagnetic particle which exhibits very high loading levels of bound substrate (see I. Sucholeiki, G. Margetts, M. Roberts, U.S. patent application Ser. No. 08/585,905).

Once the radiolabeled protein-ligand complex is separated from the unbound material, quantitation of the complex is measured by either measuring the radiation directly or by measuring the effect that the radiolabel has on a fluorescent molecule such as diphenyloxazole (DPO). The latter approach requires far less radioactivity and is more sensitive. This approach, termed scintillation, measures the fluorescent transmission of a dye solution that has been excited by a radiolabel, such as tritium or phosphorous-32. To simplify the process, the dye solution has been replaced by particles that already contain diphenyloxazole (see J. Bertoglio-Matte, U.S. Pat. No. 4,568,649). The radioactive ligand is bound to the antibody containing, particles and then exposed to the fluorescent particles. The extent of binding is determined by measuring the intensity of the fluorescence released from the fluorescent particles. This method, termed scintillation proximity assay (SPA), has the major advantage of being able measure antibody-antigen receptor binding in situ without the need for washing off unbound radioactive antibody from the particles (see H. Hart, U.S. Pat. No. 4,271,139). The problem with this method is the need for two different classes of particles. One type of particle is used to bind the antibody and another type of particle is used to attach the phosphor or photon emitting substance. Another problem with common SPA methods of analysis is the difficulty in recycling the two different types of particles in an automated fashion, since the ability to filter many assay vials simultaneously is still a major engineering challenge.

It is therefore an object of this invention to provide a radioimmunoassay technique that permits the antigens, antibodies, and the paramagnetic scintillating particles to be readily recovered for subsequent use and/or study. Another object of this invention is to provide a radioimmunoassay system that can be readily and economically automated. Still another object of this invention is to provide paramagnetic scintillating particles capable of performing three functions simultaneously: (1) To selectively bind or react labeled or unlabeled antigens with antibodies, (2) to separate the bound antigens from the unbound antigen by magnetic separation, and (3) to measure the radioactivity of the bound antigen. Lastly, it is an object of this invention to provide a radioimmunoassay technique that has the ability for measuring bound antigen on a small number of beads or even a single individual bead.

SUMMARY OF THE INVENTION

The present invention provides a novel process by which polymer coated, solvent-stable paramagnetic beads or particles can be treated both chemically and physically with a phosphor (or photon emitting substance), such as diphenyloxazole (DPO) or Rose Bengal (RB). Throughout the derivatization process, the beads can be washed of any unbound phosphor and separated by application of a magnetic field and the unbound components removed by the process of aspiration. The phosphor incorporated, paramagnetic beads are then chemically or physically coated with an antibody or protein such as, for example, the proteins streptavidin or albumin.

The present invention also provides a novel particle composition that allows for the incorporation of a high concentration of pendant functional groups per unit mass of composite particles. These pendant functional groups allow for the attachment of a high concentration of phosphor. The composite particle of the present invention comprises an outer coating of matrix material, prepared as a crosslinked polystyrene having a low degree of crosslinking and enclosing a plurality of inner particles, each of which comprises an inner matrix material, prepared as a crosslinked polystyrene with a high degree of crosslinking, capable of retaining an innermost core of magnetite. The composite particle is then coated with a protein such as albumin or streptavidin, and which becomes physically bound to the particle's outer surface.

An immunoscintillation composition and method of radioimmunoassay has been developed whereby streptavidin-coated beads are exposed to a radiolabeled antigen or ligand such as, for example, double strand DNA labeled at its 5' end with phosphorous-32 on one strand and biotin on the other. The beads are then separated from any unbound, labeled DNA by application of a magnetic field and washed with buffer. Radioactive energy released by the labeled antigen, such as phosphorous-32, excites the phosphor (or photon-emitting substance), thereby releasing bursts of fluorescent energy (photons) that are measured by a photon counting means such as a scintillation counter. Studies have established that the counted or measured photons are proportional to the concentration of labeled antigens bound to the antibodies. The level of detection is such that only a few beads are necessary for measuring the concentration of labeled antigen bound to the antibody. When the assay has been completed, the bound antigens can be released from the antibodies by elution, thus permitting the same beads or bead to be used for additional testing. These and other features and advantages of the invention will become evident from the description of preferred embodiments which follows.

DESCRIPTION OF PREFERRED EMBODIMENTS

In the context of the invention, the term paramagnetic beads is defined as follows:

The novel composite paramagnetic beads used in the present invention were obtained from Polymer Laboratories, Church Stretten, Shropshire, UK and which have been described elsewhere (see I. Sucholeiki, G. Margetts, M. Roberts, U.S. patent application Ser. No. 08/585,905 and I. Sucholeiki, U.S. patent application Ser. No. 08/462,201). The beads comprise a plurality of highly crosslinked matrix-encapsulated metal oxide particles in a low crosslinked, microporous polymer resin matrix that has the capacity for functionalization. The encapsulated metal oxide particles have a rigid polymeric coating encapsulating the metal oxide particle. The composite paramagnetic beads swell in organic solvent without losing their paramagnetic properties and provide a high surface area that can contact the solvent and that can be functionalized to allow binding to the polymeric surface, thereby providing increased capacity for binding and separating a bound component from a component in solution or suspension.

In the context of the invention, the terms antibodies and antigens are defined as follows:

Antibodies are generally recognized as having a protein-type base and, although the specification will make reference to antibodies and antigens generally, it is intended that this term also encompasses other binding materials. In this invention, two proteins, streptavidin and albumin are utilized as those materials which have a protein-type base. Antigens are meant to encompass any foreign substance that is capable of being bound to an antibody or protein. In this invention, the biotin molecule or those molecules attached to the biotin molecule function as antigens.

In order to clearly differentiate between non-specific and specific antibody-antigen binding in the radioimmunoassay, two different proteins are used. The antibody protein, streptavidin, has an affinity for the antigen, biotin, and those materials attached to the biotin molecule. Albumin is a protein that does not have a specific affinity for the antigen molecule, biotin. Paramagnetic beads having a phosphor chemically or physically attached there to are coated with either streptavidin or albumin. When the doubly labeled DNA containing phosphorous-32 and biotin is exposed to the two types of protein coated beads, those beads coated with streptavidin will produce greater photon emission, which indicates their higher binding affinity over the albumin-coated beads.

In the context of this invention, the term labeled antigens is defines as follows:

Labeled antigens are foreign substances that have been altered to include a radioisotope. Double strand DNA, doubly labeled at its 5' ends with phosphorous-32 on one strand and biotin on the other, acts in this invention as the antigen and was synthesized as follows:

A 20-mer primer (obtained from Synthetic Genetics) was labeled with Phosphorous-32 using gamma-phosphorous-32-ATP(obtained from Dupont) and T4 Kinase (obtained from USB). The 5'-phosphorous-32 labeled primer, combined with 5'-biotin labeled primer (obtained from Ransom Hill Biosciences), was used in the polymerase chain reaction (PCR) to produce crude doubly labeled DNA. The crude PCR product was then purified by polyacrylamide gel electrophoresis (PAGE) to give a 10.0 microCurie/mL solution of doubly labeled DNA.

In the context of the invention, the term scintillation counter is defined as follows:

The scintillation counter consist of three essential parts: 1) a scintillation phosphor, 2) a photomultiplier, and 3) an optical reporting system. In this invention, one of two organic phosphors is used, diphenyloxazole (DPO) or Rose Bengal (RB). The scintillation counter used in this invention is a Beckman LS 1801 liquid scintillation counter.

The magnetic separation procedure of this invention is as follows:

Paramagnetic composite particles, both protein-coated and uncoated, were separated from any solvent in which they were suspended by applying a magnetic field gradient using a neodymium magnet obtained from Master Magnetics, Castle Rock, Co. The neodymium magnetic was applied to the side of the Eppendorf tube or reaction vessel, resulting in the particles aggregating along the inner surface of the tube or vessel adjacent the position of the magnet. The solvent or buffer was then siphoned or pipetted off. The neodymium magnet was removed, fresh solvent was added, and the mixture was shaken.

In order to further specify the process of this invention, the following examples are provided. It will be recognized by those skilled in the art that these examples represent only specific implementations of the process of the invention. They in no way limit its scope.

EXAMPLE 1

Synthesis of Diphenyloxazole (DPO) Containing Paramagnetic Beads To 0.7 grams of polystyrene coated paramagnetic beads incorporating chloromethyl functional groups (obtained from Polymer Laboratories, Church Stretten, Shropshire, UK and exhibiting a substitution of 0.96 mmoles Cl/gram of beads) was added 10 mL of a 20% dimethylsulfoxide (DMSO) solution of 2,5-diphenyloxazole (DPO) obtained from Aldrich Chemicial Company, Milwaukee, Wis. The mixture was shaken at room temperature for 24 hours. At the end of 24 hours, the mixture was transferred to a large beaker containing 1 liter of deionized water and stirred for 10 minutes. The white precipitant was decanted off. This was repeated three more times. The beads were then washed four times with methanol and decanted and then placed under pump vacuum for 24 hours to give 0.4 grams of diphenyloxazole containing paramagnetic beads. Elemental analysis of the beads gave a chlorine substitution of 0.80 mmoles chlorine/gram of beads and a nitrogen substitution of 0.93 mmoles nitrogen/gram (which is equal to 0.46 mmoles of DPO/gram of beads).

EXAMPLE 2

Synthesis of Covalently Bound Rose Bengal (RB) Paramagnetic Beads. To a vial was added 1.0 grams of chloromethylated magnetic beads, and 2.0 grams of Rose Bengal, and 20 mL of dimethylformamide. The mixture was sonicated using a Heat Systems Sonicator, model XL2020 for a total of 8 hours then filtered and sequentially washed with DMF, methanol, THF, and methylene chloride, with the last wash ending with methanol. The beads were then placed under vacuum overnight to give 1.0 gram of red rose bengal-coupled magnetic composite particles. Iodine elemental analysis gave a loading of 0.092 mmoles iodine/gram particles (equivalent to 0.023 mmoles rose bengal/gram particles).

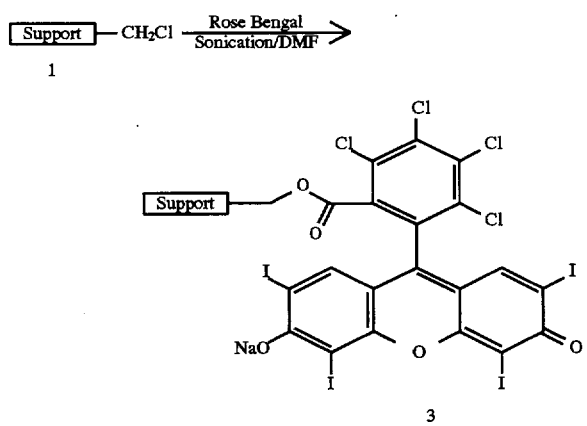

EXAMPLE 3

Streptavidin Binding to DPO Paramagnetic Beads. To 4.6 mg of DPO paramagnetic beads in an Eppendorf tube was added 0.25 mg of streptavidin (obtained from Boehringer/Mannheim with molecular weight of approx. 60,000) dissolved in 1 mL of 0.1M phosphate buffered saline (PBS). The mixture was rotated at room temperature using a Labquake Shaker for 24 hours. After 24 hours, the beads were centrifuged using a Eppendorf Centrifuge 5415C for 3–4 minutes. A neodymium magnet (obtained from Master Magnetics, Castle Rock, Colo.) was placed to the side of the Eppendorf tube, causing the beads to aggregate along the inner surface of the tube adjacent the position of magnet. The liquid was removed using a Pasteur pipette. To the beads were then added 1 mL of PBS and the mixture was shaken for 10 minutes. The tube was then centrifuged and the neodymium magnetic was again applied to the side of the tube and the liquid removed using a Pasteur pipette. The beads were washed following the same protocol an additional two more times.

EXAMPLE 4

Streptavidin Binding to RB Paramagnetic Beads. To 4.7 mg of RB paramagnetic beads in an Eppendorf tube was added 0.25 mg of streptavidin (obtained from Boehringer/Mannheim with molecular weight of approx. 60,000) dissolved in 1 mL of 0.1M phosphate buffered saline (PBS) The mixture was rotated at room temperature using a Labquake Shaker for 24 hours. After 24 hours the beads were centrifuged using an Eppendorf Centrifuge 5415C for 3–4 minutes. A neodymium magnet (obtained from Master Magnetics, Castle Rock, Colo.) was placed to the side of the Eppendorf tube, causing the beads to aggregate along the inner surface of the tube adjacent the position of the magnet. The liquid was removed using a Pasteur pipette. To the beads were then added 1 mL of PBS and mixture shaken for 10 minutes. The tube was then centrifuged and the neodymium magnet was again applied to the side of the tube and the liquid removed using a Pasteur pipette. The beads were washed following the same protocol an additional two more times.

EXAMPLE 5

Albumin Binding to DPO-Paramagnetic Beads. To 5.0 mg of DPO-Paramagnetic beads was added 3 mg of albumin (obtained from Sigma Chemical Co.) in 1 mL of 0.1M phosphate buffered saline (PBS). The mixture was rotated at room temperature using a Labquake Shaker for 24 hours. After 24 hours the beads were centrifuged using a Eppendorf Centrifuge 5415C for 3-4 minutes. A neodymium magnet (obtained from Master Magnetics, Castle Rock, Co.) was placed to the side of the Eppendorf tube, causing the beads to aggregate along the inner surface of the tube adjacent the position of the magnet. The liquid was removed using a Pasteur pipette. To the beads were then added 1 mL of PBS and mixture shaken for 10 minutes. The tube was then centrifuged and the neodymium magnet was again applied to the side of the tube and the liquid removed using a Pasteur pipette. The beads were washed following the same protocol an additional two more times.

EXAMPLE 6

Binding of Doubly Labeled DNA to Avidin-Coated DPO-paramagnetic Beads. To 4.6 mg of avidin-coated DPO-paramagnetic beads was added 1 mL of 1M NaCl solution and 10 microliters of a 10 microCurie/mL solution of doubly labeled DNA. The mixture was then shaken at 55° C. for 20 minutes using a thermomixer. The beads were then washed of non-specific ligand binding by first centrifuging the Eppendorf tube and then exposing the side of the tube to a neodymium magnet (obtained from Master Magnetics, Castle Rock, Colo.), causing the beads to aggregate along the inner surface of the tube adjacent the position of the magnet. The liquid was removed using a Pasteur pipette. To the beads were then added 1 mL of 1M NaCl solution and mixture vortexed for 20 seconds. The tube was then centrifuged and the neodymium magnet was again applied to the side of the tube and the liquid removed using a Pasteur pipette. The beads were washed following the same protocol an additional two more times.

After the beads were counted using scintillation, a batch consisting of 17 beads was removed and counted and then one individual bead was removed and counted (See Table 1 and Table 3).

EXAMPLE 7

Binding of Doubly Labeled DNA to plain DPO-paramagnetic Beads. To 4.5 mg of DPO-paramagnetic beads was added 1 mL of 1M NaCl solution and 10 microliters of a 10 microCurie/mL solution of doubly labeled DNA. The mixture was then shaken at 55 OC for 20 minutes using a thermomixer. The beads were then washed of non-specific ligand binding by first centrifuging the Eppendorf tube and then exposing the side of the tube to a neodymium magnet (obtained from Master Magnetics, Castle Rock, Colo.) causing the beads to aggregate along the inner surface of the tube adjacent the position of the magnet. The liquid was removed using a Pasteur pipette. To the beads were then added 1 mL of 1M NaCl solution and the mixture was vortexed for 20 seconds. The tube was then centrifuged and the neodymium magnet was again applied to the side of the tube and the liquid removed using a Pasteur pipette. The beads were washed following the same protocol an additional two more times.

After the beads were counted using scintillation, a batch consisting of 17 beads was removed and counted and then one individual bead was counted (see Table 1 and Table 3).

EXAMPLE 8

Binding of Doubly Labeled DNA to Avidin-Coated RB-paramagnetic Beads. To 4.7 mg of avidin-coated RB-paramagnetic beads was added 1 mL of 1M NaCl solution and 10 microliters of a 10 microCurie/mL solution of doubly labeled DNA. The mixture was then shaken at 55° C. for 20 minutes using a thermomixer. The beads were then washed of non-specific ligand binding by first centrifuging the Eppendorf tube and then exposing the side of the tube to a neodymium magnet (obtained from Master Magnetics, Castle Rock, Colo.) causing the beads to aggregate along the inner surface of the tube adjacent the position of the magnet. The liquid was removed using a Pasteur pipette. To the beads were then added 1 mL of 1M NaCl solution and the mixture was vortexed for 20 seconds. The tube was then centrifuged and the neodymium magnet was again applied to the side of the tube and the liquid removed using a Pasteur pipette. The beads were washed following the same protocol an additional two more times.

After the beads were counted using scintillation, a batch consisting of 17 beads was removed and counted and then one individual bead was counted (see Table 2 and Table 4).

EXAMPLE 9

Binding of Doubly Labeled DNA to plain RB-paramagnetic Beads. To 4.8 mg of RB-paramagnetic beads was added 1 mL of 1M NaCl solution and 10 microliters of a 10 microcurie/mL solution of doubly labeled DNA. The mixture was then shaken at 55° C. for 20 minutes using a thermomixer. The beads were then washed of non-specific ligand binding by first centrifuging the Eppendorf tube and then exposing the side of the tube to a neodymium magnet (obtained from Master Magnetics, Castle Rock, Colo.) causing the beads to aggregate along the inner surface of the tube adjacent the position of the magnet. The liquid was removed using a Pasteur pipette. To the beads were then added 1 mL of 1M NaCl solution and mixture vortexed for 20 seconds. The tube was then centrifuged and the neodymium magnet was again applied to the side of the tube and the liquid removed using a Pasteur pipette. The beads were washed following the same protocol an additional two more times.

After the beads were counted using scintillation, a batch consisting of 17 beads was removed and counted and then one individual bead was counted (see Table 2 and Table 4).

EXAMPLE 10

Binding of Doubly Labeled DNA to Albumin-Coated DPO-paramagnetic Beads. To 5 mg of albumin-coated DPO-paramagnetic beads was added 1 mL of 1M NaCl solution and 10 microliters of a 10 microCurie/mL solution of doubly labeled DNA. The mixture was then shaken at 55° C. for 20 minutes using a thermomixer. The beads were then washed of non-specific ligand binding by first centrifuging the Eppendorf tube and then exposing the side of the tube to a neodymium magnet (obtained from Master magnetics, Castle Rock, Colo.) causing the beads to aggregate along the inner surface of the tube adjacent the position of the magnet. The liquid was removed using a Pasteur pipette. To the beads were then added 1 mL of 1M NaCl solution and mixture vortexed for 20 seconds. The tube was then centrifuged and the neodymium magnet was again applied to the side of the tube and the liquid removed using a Pasteur pipette. The beads were washed following the same protocol an additional two more times.

After the beads were counted using scintillation, a batch consisting of 17 beads was removed and counted and then one individual bead was removed and counted (see Table 1 and Table 3).

TABLE I

Scintillation of DNA-Bound DPO-Paramagnetic Beads In 2 mL 1 M NaCl Solution Using A Beckman LS 1801 Liquid Scintillation Counter.

| Type Of Bead | Quantity | Counts Per Minute (Average Of Three Trials) |
| --- | --- | --- |
| Plain DPO-paramagnetic beads | 4.5 mg | 46 |
| Albumin-coated DPO-paramagnetic beads | 5.0 mg | 80 |
| Avidin-coated DPO-paramagnetic beads | 4.6 mg | 353 |
| Plain DPO-paramagnetic beads | 17 beads (1 mg) | 32 |
| Albumin-coated DPO-paramagnetic beads | 17 beads | 32 |
| Avidin-coated DPO-paramagnetic beads | 17 beads | 56 |
| Plain DPO-paramagnetic beads | 1 bead | 25 |
| Albumin-coated DPO-paramagnetic beads | 1 bead | 17 |
| Avidin-coated DPO-paramagnetic beads | 1 bead | 27 |

TABLE II

Scintillation Of DNA-Bound RB-Paramagnetic Beads In 2 mL 1 M NaCl Solution Using A Beckman LS 1801 Liquid Scintillation Counter.

| Type Of Bead | Quantity | Counts Per Minute (Average of Three Trials) |
| --- | --- | --- |
| Plain RB-paramagnetic beads | 4.8 mg | 88 |
| Avidin-coated RB-paramagnetic beads | 4.7 mg | 1406 |
| Plain RB-paramagnetic beads | 17 beads (1 mg) | 41 |
| Avidin-coated RB-paramagnetic beads | 17 beads | 108 |
| Plain RB-paramagnetic beads | 1 bead | 24 |
| Avidin-coated RB-paramagnetic beads | 1 bead | 28 |

TABLE III

Scintillation Of DNA-Bound DPO-Paramagnetic Bead Using A Beckman LS 1801 Liquid Scintillation Counter Without Solvent.

| Type Of Bead | Quantity | Counts Per Minute (Average Of Three Trials) |
| --- | --- | --- |
| Plain DPO-paramagnetic beads | 4.5 mg | 26 |
| Albumin-coated DPO-paramagnetic beads | 5.0 mg | 82 |
| Avidin-coated DPO-paramagnetic beads | 4.6 mg | <u>339</u> |

TABLE IV

Scintillation Of DNA-Bound RB-Paramagnetic Bead Using A Beckman LS 1801 Liquid Scintillation Counter Without Solvent.

| Type Of Bead | Quantity | Counts Per Minute (Average Of Three Trials) |
| --- | --- | --- |
| Plain RB-paramagnetic beads | 4.8 mg | 105 |
| Avidin-coated RB-paramagnetic beads | 4.7 mg | <u>1185</u> |

I claim:

1. An immunoscintillation composition comprising:
   (a) at least one magnetically responsive composite particle comprising
      (i) a resin matrix that defines a composite particle outer surface region defining a plurality of pores therethrough, said pores being limited in their diameter such that said resin matrix is capable of retaining a plurality of inner particles therein,
      (ii) a plurality of inner particles retained in said resin matrix, each of said inner particles comprising a resin shell such that said inner particle resin shell is capable of retaining a solid, non-resin core, and
      (iii) a like plurality of solid, non-resin cores comprising a magnetically responsive material, each of said solid, non-resin cores being retained in said inner particle resin shell,
   (b) a photon-emitting substance that is attached to said at least one magnetically responsive composite particle; and
   (c) an immunoadsorbent capable of binding labeled and unlabeled antigens, said immunoadsorbent being provided on said composite particle outer surface region.

2. The immunoscintillation composition of claim 1 wherein the outer resin matrix is composed of loosely-crosslinked polymer.

3. The immunoscintillation composition of claim 1 wherein the inner resin matrix is composed of highly-crosslinked polymer.

4. The immunoscintillation composition of claim 1 wherein said composite particle surface region is capable of accommodating a plurality of pendant functional groups bound thereto, such that said composite particle may have photon-emitting substances attached thereto.

5. The immunoscintillation composition of claim 1 wherein the magnetically responsive material is selected from the group consisting of paramagnetic and superparamagnetic materials.

6. The immunoscintillation composition of claim 5 wherein the magnetically responsive material is magnetite.

7. The immunoscintillation composition of claim 4 wherein the photon emitting substance is a scintillation phosphor.

8. The immunoscintillation composition of claim 7 wherein the scintillation phosphor is diphenyloxazole.

9. The immunoscintillation composition of claim 7 wherein the scintillator phosphor is rose bengal.

10. The immunoscintillation composition of claim 1 wherein the immunoadsorbent is selected from the group consisting of antibodies and proteins.

11. The immunoscintillation composition of claim 10 wherein the immunoadsorbent is streptavidin.

12. The immunoscintillation composition of claim 10 wherein the immunoadsorbent is albumin.

13. The immunoscintillation composition of claim 1 wherein the photon-emitting substance is a solid scintillation phosphor.

14. The immunoscintillation composition of claim 1 wherein the immunoadsorbent is an antibody.

15. The immunoscintillation composition of claim 1 wherein the labeled bodies have phosphorous-32 bound thereto.

16. The immunoscintillation composition of claim 1 wherein the labeled and unlabeled bodies are biotin-containing molecules.

17. The immunoscintillation composition of claim 7 wherein the biotin-containing molecule is a doubly stranded DNA.

18. An immunoscintillation composition comprising a composite, magnetically responsive resin particle composed of an outer resin matrix enclosing a plurality of inner particles, each of said inner particles comprising a resin shell enclosing a solid, non-resin core, said solid, non-resin core comprising a paramagnetic or superparamagnetic material, and said composite resin particle bearing a plurality of pendant functional groups in high concentration.

19. A method of radioimmunoassay comprising the steps of:
   (a) providing a vessel having an outer surface, an inner surface, and a fluid medium contained therein;
   (b) suspending in said fluid medium in said vessel an immunoscintillation composition comprising:
      (i) at least one magnetically responsive composite particle comprising
         (1) a resin matrix that defines a composite particle outer surface region defining a plurality of pores therethrough, said pores being limited in their diameter such that said resin matrix is capable of retaining a plurality of inner particles therein,
         (2) a plurality of inner particles retained in said resin matrix, each of said inner particles comprising a resin shell such that said inner particle resin shell is capable of retaining a solid, non-resin core, and
         (3) a like plurality of solid, non-resin cores comprising a magnetically responsive material, each of said solid, non-resin cores being retained in said inner particle resin shell,
      (ii) a photon-emitting substance that is attached to said at least one magnetically responsive composite particle; and
      (iii) an immunoadsorbent capable of binding labeled and unlabeled antigens, said immunoadsorbent being provided on said composite particle outer surface region;
   (c) adding to the suspension labeled antigens capable of specifically biochemically binding to said immunosorbent on said particles, said labeled antigens emitting radiation energy capable of activating said photon-emitting substance such that, upon binding of the labeled antigens to said immunosorbent, said emitted radiation energy activates said photon-emitting substance;

(d) separating said immunoscintillation composition from said fluid medium by means of applying a magnetic field to a location adjacent one portion of said vessel outer surface so that said composition aggregates along the corresponding inner surface of said vessel opposite said magnetic field location and subsequent aspiration of said fluid medium;

(e) washing said particles with a fresh solvent capable of removing from said immunoscintillation composition any unbound labeled antigens;

(f) separating said washed immunoscintillation composition from said fresh solvent containing any unbound labeled antigens, as in step (d), above;

(g) resuspending said washed immunoscintillation composition by adding new fresh solvent thereto;

(h) measuring the light energy emitted by said photon-emitting substance attached to said suspended immunoscintillation composition.

20. The method of radioimmunoassay as claimed in claim 19, wherein said separation and washing steps (d) to (e) are repeated at least once.

21. A method of radioimmunoassay comprising the steps of:

(a) providing a vessel having an outer surface, an inner surface, and a fluid medium contained therein;

(b) suspending in said fluid medium in said vessel an immunoscintillation composition comprising:
  (i) at least one magnetically responsive composite particle comprising
    (1) a resin matrix that defines a composite particle outer surface region defining a plurality of pores therethrough, said pores being limited in their diameter such that said resin matrix is capable of retaining a plurality of inner particles therein,
    (2) a plurality of inner particles retained in said resin matrix, each of said inner particles comprising a resin shell such that said inner particle resin shell is capable of retaining a solid, non-resin core, and
    (3) a like plurality of solid, non-resin cores comprising a magnetically responsive material, each of said solid, non-resin cores being retained of a said inner particle resin shell,
  (ii) a photon-emitting substance that is attached to said at least one magnetically responsive composite particle; and
  (iii) an immunoadsorbent capable of binding labeled and unlabeled antigens, said immunoadsorbent being provided on said composite particle outer surface region;

(c) adding to the suspension labeled antigens capable of specifically biochemically binding to said immunosorbent on said particles, said labeled antigens emitting radiation energy capable of activating said photon-emitting substance such that, upon binding of the labeled antigens to said immunosorbent, said emitted radiation energy activates said photon-emitting substance;

(d) separating said immunoscintillation composition from said fluid medium by means of applying a magnetic field to a location adjacent one portion of said vessel outer surface so that said composition aggregates along the corresponding inner surface of said vessel opposite said magnetic field location and subsequent aspiration of said fluid medium;

(e) washing said particles with a fresh solvent capable of removing from said immunoscintillation composition any unbound labeled antigens;

(f) separating said washed immunoscintillation composition from said fresh solvent containing any unbound labeled antigens, as in step (d), above;

(g) measuring the light energy emitted by said photon-emitting substance attached to said unsuspended immunoscintillation composition.

22. The method of radioimmunoassay as claimed in claim 21, wherein said separation and washing steps (d) to (e) are repeated at least once.

23. A method of radioimmunoassay comprising the steps of:

(a) providing a vessel having an outer surface, an inner surface, and a fluid medium contained therein;

(b) suspending in said fluid medium in said vessel an immunoscintillation composition comprising:
  (i) at least one magnetically responsive composite particle comprising
    (1) a resin matrix that defines a composite particle outer surface region defining a plurality of pores therethrough, said pores being limited in their diameter such that said resin matrix is capable of retaining a plurality of inner particles therein,
    (2) a plurality of inner particles retained in said resin matrix, each of said inner particles comprising a resin shell such that said inner particle resin shell is capable of retaining a solid, non-resin core, and
    (3) a like plurality of solid, non-resin cores comprising a magnetically responsive material, each of said solid, non-resin cores being retained in said inner particle resin shell,
  (ii) diphenyloxazole attached to said at least one magnetically responsive composite particle; and
  (iii) an immunoadsorbent capable of binding labeled and unlabeled antigens, said protein being provided on said composite particle outer surface region;

(c) adding to the suspension molecules that are radiolabeled and that are capable of specifically biochemically binding to said immunoadsorbent on said immunoscintillation composition, said labeled molecules emitting radiation energy capable of activating said diphenyloxazole such that, upon binding of the labeled molecule to said immunoadsorbent, said emitted radiation energy activates said diphenyloxazole;

(d) separating said immunoscintillation composition from said fluid medium by means of applying a magnetic field to a location adjacent one portion of said vessel outer surface so that said composition aggregates along the corresponding inner surface of said vessel opposite said magnetic field location and subsequent aspiration of said fluid medium;

(e) washing said particles with a fresh solvent capable of removing from said immunoscintillation composition any unbound labeled molecules;

(f) separating said washed immunoscintillation composition from said fresh solvent containing any unbound labeled molecules, as in step (d), above;

(g) resuspending said washed immunoscintillation composition by adding new fresh solvent thereto;

(h) measuring the light energy emitted by said diphenyloxazole attached to said suspended immunoscintillation composition.

24. The method of radioimmunoassay as claimed in claim 23, wherein said separation and washing steps (d) to (e) are repeated at least once.

25. A method of radioimmunoassay comprising the steps of:

(a) providing a vessel having an outer surface, an inner surface, and a fluid medium contained therein;

(b) suspending in said fluid medium in said vessel an immunoscintillation composition comprising:

(i) at least one magnetically responsive composite particle comprising (1) a resin matrix that defines a composite particle outer surface region defining a plurality of pores therethrough, said pores being limited in their diameter such that said resin matrix is capable of retaining a plurality of inner particles therein, (2) a plurality of inner particles retained in said resin matrix, each of said inner particles comprising a resin shell such that said inner particle resin shell is capable of retaining a solid, non-resin core, and (3) a like plurality of solid, non-resin cores comprising a magnetically responsive material, each of said solid, non-resin cores being retained in said inner particle resin shell, (ii) Rose Bengal attached to said at least one magnetically responsive composite particle; and (iii) an immunoadsorbent capable of binding labeled and unlabeled antigens, said protein being provided on said composite particle outer surface region;

(c) adding to the suspension molecules that are radiolabeled and that are capable of specifically biochemically binding to said immunoadsorbent on said immunoscintillation composition, said labeled molecules emitting radiation energy capable of activating said Rose Bengal such that, upon binding of the labeled molecule to said immunoadsorbent, said emitted radiation energy activates said Rose Bengal;

(d) separating said immunoscintillation composition from said fluid medium by means of applying a magnetic field to a location adjacent one portion of said vessel outer surface so that said composition aggregates along the corresponding inner surface of said vessel opposite said magnetic field location and subsequent aspiration of said fluid medium;

(e) washing said particles with a fresh solvent capable of removing from said immunoscintillation composition any unbound labeled molecules;

(f) separating said washed immunoscintillation composition from said fresh solvent containing any unbound labeled molecules, as in step (d), above;

(g) resuspending said washed immunoscintillation composition by adding new fresh solvent thereto;

(h) measuring the light energy emitted by said Rose Bengal attached to said suspended immunoscintillation composition.

26. The method of radioimmunoassay as claimed in claim 25, wherein said separation and washing steps (d) to (e) are repeated at least once.

* * * * *